(12) United States Patent
Cai et al.

(10) Patent No.: US 10,703,720 B2
(45) Date of Patent: Jul. 7, 2020

(54) METHOD FOR PREPARING CHROMIUM(III) PYRIDINE-2-CARBOXYLATE USING 2-OP RECTIFICATION RESIDUES

(71) Applicant: YANCHENG INSTITUTE OF TECHNOLOGY, Yancheng, Jiangsu (CN)

(72) Inventors: Zhaosheng Cai, Jiangsu (CN); Jinghua Yu, Jiangsu (CN); Pan Xu, Jiangsu (CN); Jinyu Bian, Jiangsu (CN); Ge Ding, Jiangsu (CN); Lili Shen, Jiangsu (CN); Xujuan Huang, Jiangsu (CN); Zhonglie Yang, Jiangsu (CN); Yun Chen, Jiangsu (CN); Peng Xu, Jiangsu (CN)

(73) Assignee: YANCHENG INSTITUTE OF TECHNOLOGY, Yangcheng (CN)

( * ) Notice: Subject to any disclaimer, the term of this patent is extended or adjusted under 35 U.S.C. 154(b) by 0 days.

(21) Appl. No.: 16/452,488

(22) Filed: Jun. 25, 2019

(65) Prior Publication Data

US 2020/0109116 A1    Apr. 9, 2020

(51) Int. Cl.
*C07D 213/50* (2006.01)
*C07F 11/00* (2006.01)

(52) U.S. Cl.
CPC .......... *C07D 213/50* (2013.01); *C07F 11/005* (2013.01); *C07B 2200/13* (2013.01)

(58) Field of Classification Search
CPC .............................. C07D 213/50; C07F 11/005
See application file for complete search history.

(56) References Cited

U.S. PATENT DOCUMENTS 5,702,930 A * 12/1997 Kiener ................... C12P 17/12
435/122

FOREIGN PATENT DOCUMENTS

| CN | 101602716 B | 5/2011 |
| CN | 103319401 A | 9/2013 |
| CN | 105541707 A | 5/2016 |

* cited by examiner

*Primary Examiner* — Noble E Jarrell
(74) *Attorney, Agent, or Firm* — Wayne & Ken, LLC; Tony Hom

(57) ABSTRACT

A method for preparing chromium(III) pyridine-2-carboxylate using 2-OP rectification residues, including: subjecting the 2-OP rectification residues to in-situ catalytic pyrolysis and vacuum distillation, room-temperature crystallization and separation, recrystallization and dehydration, alkali-catalyzed hydrolysis, acidification and complexation, and separation, washing and drying to prepare a chromium(III) pyridine-2-carboxylate product, of which a yield is greater than 50% of the weight of the 2-OP rectification residues. The acidification and complexation includes: cooling the aqueous solution containing sodium pyridine-2-carboxylate obtained from the alkali-catalyzed hydrolysis to a temperature below 50° C.; adjusting the aqueous solution to pH 3.0-8.5 with 5-50 wt % dilute $H_2SO_4$ or 3-30 wt % dilute HCl followed by batchwise addition of $CrCl_3$, $Cr(NO_3)_3$ or $Cr_2(SO_4)_3$ for complexation at 20-70° C. to obtain a slurry containing chromium(III) pyridine-2-carboxylate, which is separated, washed and dried to obtain a chromium(III) pyridine-2-carboxylate product with a purity of 98.5% or more.

11 Claims, 2 Drawing Sheets

METHOD FOR PREPARING CHROMIUM(III) PYRIDINE-2-CARBOXYLATE USING 2-OP RECTIFICATION RESIDUES

CROSS REFERENCE TO RELATED APPLICATIONS

This application claims the benefit of priority from Chinese Patent Application No. 201811221062.X, filed on Oct. 8, 2018. The content of the aforementioned application, including any intervening amendments thereto, is incorporated herein with reference in its entirety.

TECHNICAL FIELD

The application relates to organic synthesis, particularly to a new method of recycling and efficiently utilizing chemical by-products in the preparation of fine organic chemicals, and more particularly to a method of preparing chromium (III) pyridine-2-carboxylate using 2-OP rectification residues.

BACKGROUND

2-OP, also chemically named 2-cyanopyridine, pyridine-2-carbonitrile and 2-pyridinecarbonitrile and with a CAS Number of 100-70-9, is a white to light brown needle-like crystal having a melting point of 24~27° C. As an important intermediate, 2-OP has been widely used in the synthesis of various fine organic chemicals such as pharmaceuticals, agrochemicals and dyes, and most of these chemicals exhibit various excellent properties. For example, the new herbicide picloram prepared from the 2-OP has the advantages of high efficacy, good selectivity, low toxicity and small residual amount and short residual period in soil and plant, suitable for the control of the most dicotyledonous weeds and shrubs in the fields of wheat, corn and sorghum. Moreover, the 2-OP can also be used to synthesize 2-amino-5-chloropyridine which is an important intermediate in the manufacture of a novel oral anticoagulant betrixaban.

There are several methods of synthesizing the 2-OP, including catalytic 2-methylpyridine ammoxidation method, cyano substitution method, pyridine-2-carboxaldoxime method and 2-aminopyridine method. Regarding the catalytic 2-methylpyridine ammoxidation method, a mixture of nitrogen and oxygen is used as an oxidant to directly oxidize the 2-methylpyridine into the 2-OP at high temperature in the presence of a catalyst. In the cyano substitution method, 2-halopyridine is reacted with acetone cyanohydrin and an inorganic alkali metal cyanide under a certain condition to enable the substitution of the halogen atom with a cyano group to form the 2-OP. As for the pyridine-2-carboxaldoxime method, pyridine-2-carboxaldoxime is directly dehydrated in the presence of a dehydrating agent or hydrated at high temperature to give the 2-OP. In the 2-aminopyridine method, the 2-aminopyridine is diazotized to form a pyridine diazonium salt, which subsequently undergoes Sandmeyer reaction with cuprous cyanide to produce the 2-OP. The catalytic 2-methylpyridine ammoxidation method emerges from such methods and is widely used in actual production because of sufficient source, absence of highly-toxic cyanide, high safety and less cost.

There are two conversion pathways in the preparation of the 2-OP using the catalytic 2-methylpyridine ammoxidation in the presence of high temperature and a catalyst. In one pathway, 2-methylpyridine is oxidized into pyridine-2-carboxaldehyde in the presence of a catalyst, and then the pyridine-2-carboxaldehyde is reacted with ammonia to form pyridine-2-methylenimine which is dehydrogenated to produce the 2-OP. While in the other pathway, after 2-methylpyridine is oxidized into pyridine-2-carboxaldehyde in the presence of a catalyst, the pyridine-2-carboxaldehyde is continuously oxidized into pyridine-2-carboxylic acid, which is then reacted with ammonia at high temperature to form pyridine-2-carboxamide. The pyridine-2-carboxamide is subsequently dehydrated at high temperature to produce the 2-OP. Actually, in the process of preparing the 2-OP from 2-methylpyridine by catalytic ammoxidation, the oxidized product is generally required to be rectified to obtain the 2-OP with high purity, while a large amount of rectification residue is simultaneously generated, the amount of which is about 10%-15% of the 2-OP production. Currently, the residues formed in the rectification are treated as a hazardous solid waste, and are subjected to harmless treatment by high-temperature incineration and then landfilled or mineralized. However, such a treatment requires a large amount of energy and often fails to obtain the absolutely harmless rectification residues. In addition, some fine chemicals such as pyridine-2-carboxamide and pyridine-2-carboxaldehyde may exist in the rectification residues derived from the process of preparing the 2-OP from 2-methylpyridine by the catalytic ammoxidation, so the high-temperature incineration treatment may result in insufficient utilization of the residues.

Chromium(III) pyridine-2-carboxylate, also named pyridine-2-carboxylic acid chromium(III) salt, chromium(III) 2-pyridinecarboxylate, chromium(III) picolinate, tris (picolinate) chromium(III) and picolinic acid chromium(III) salt and with CAS Number of 14639-25-9, is a violet to purplish red crystalline powder, which can succeed in passing through the cell membrane and directly act on tissue cells, enhancing the activity of insulin and improving the glycometabolism.

Chromium(III) pyridine-2-carboxylate is chemically stable at room temperature, slightly soluble in water and insoluble in ethanol. Additionally, chromium(III) pyridine-2-carboxylate has electrically-neutral molecular structure and hydrophobicity, so that it can undergo the transmembrane absorption in a complete structure. The GTF (Glucose Tolerance Factor)-like structure of chromium(III) pyridine-2-carboxylate can facilitate its absorption and the exertion of its biological functions. Moreover, chromium(III) pyridine-2-carboxylate is a supplement which plays a role in strengthening muscles and losing weight, and it can also increase the amount of active AMP protein kinase (AMPK) involving in metabolic pathways in skeletal muscle cells, improving the energy balance and functions of the insulin. As a feed additive, chromium(III) pyridine-2-carboxylate can not only increase the proportion of lean meat, reduce fat content and improve the carcass quality, but also enhance the animals' anti-stress ability and immunity, thereby promoting the yield of animal products. In August 2005, the US Food and Drug Administration (FDA) approved the production of chromium(III) pyridine-2-carboxylate, and confirmed that it is safe to apply chromium(III) pyridine-2-carboxylate in the treatment of insulin resistance type II diabetes.

There are four primary methods of preparing chromium (III) pyridine-2-carboxylate. In method 1, pyridine-2-carboxylic acid is reacted with potassium hydroxide in ethanol to form potassium pyridine-2-carboxylate which is then reacted with chromium trichloride dissolved in ethanol to produce chromium(III) pyridine-2-carboxylate. In method 2, pyridine-2-carboxylic acid is reacted with sodium hydroxide in water to form sodium pyridine-2-carboxylate which is then reacted with chromium(III) nitrate to produce chromium(III) pyridine-2-carboxylate. In method 3, 2-methylpyridine is oxidized by chromic anhydride into pyridine-2-carboxylic acid in the presence of sulfuric acid and then the pyridine-2-carboxylic acid is complexed with trivalent chromium under acidic conditions to produce chromium(III) pyridine-2-carboxylate, where the excessive chromic anhydride is removed by ethanol reduction and the excess trivalent chromium is removed by alkalization. The key step in this method is to oxidize the methyl in the 2-methylpyridine into a carboxyl group. In method 4, 2-methylpyridine is oxidized by potassium permanganate into pyridine-2-carboxylic acid followed by filtration to remove $MnO_2$ and complexation to produce chromium(III) pyridine-2-carboxylate.

The application discloses a method of preparing chromium(III) pyridine-2-carboxylate using 2-OP rectification residues, which relates to a cleaner production technology in the high-value utilization and reduction of chemical hazardous solid wastes.

In order to develop a method of preparing chromium(III) pyridine-2-carboxylate using 2-OP rectification residues, the references are made to many publications related to the preparation, application and analysis of pyridine-2-carbonitrile, pyridine-2-carboxylic acid and chromium(III) pyridine-2-carboxylate; for example, Transition metal-free synthesis of primary amides from aldehydes and hydroxylamine hydrochloride, *Tetrahedron Letters*, 2014, Vol. 55, No. 20; Progress in preparation of pyridinecarboxylic acids, *Chemical Research and Applications*, 2003, Vol. 15, No. 2; Synthesis of 3,6-dichloropicolinic acid, *CIESC Journal*, 2011, Vol. 62, No. 9; Electrochemical synthesis of 3,6-dichloropicolinic acid and its industrialization, *CIESC Journal*, 2010, Vol. 61, No. 3; Synthesis and characterization of cobalt(II) and nickel(II) complexes of 2-picolinic acid by room temperature solid-solid reaction, *Fine Chemicals*, 2013, Vol. 30, No. 3; Synthesis and application of nicotinic acid, Applied Chemical Industry, 2010, Vol. 39, No. 10; Study on V—Ti—O—Mo catalysts for 2-cyanopyridine synthesis via gas-solid ammoxidation, *Journal of Chemical Engineering of Chinese Universities*, 2016, Vol. 30, No. 4; Improvement on the technologic process of synthesis of 2-pyridinecarboxylic acid, *Hubei Chemical Industry*, 2001, Vol. 18, No. 2; Synthesis of 2-pyridinecarboxylic acid by oxidation with $KMnO_4$, *Chemical Research*, 2010, Vol. 21, No. 1; Synthesis of 2-pyridinecarboxylic acid oxidation of potassium dichromate, *Journal of Molecular Science*, 2007, Vol. 23, No. 2; Technology improvement of chromium 2-picolinate, *Hebei Journal of Industrial Science & Technology*, 2015, Vol. 32, No. 6; Improved synthesis of chromium 2-picolinate, *Feed Industry*, 2001, Vol. 22, No. 5; Synthesis and biological activity of chromium pyridine carboxylates, *Chemical Reagents*, 2001, Vol. 23, No. 6; A new process of synthesis of chromium-2-picolinate by chromic anhydride oxidation, *Chemical Engineer*, 2005, No. 9; Ammonia oxidation catalytic synthesis of 2-cyanopyrazine, *Journal of Chemistry and Chemical Engineering*, 2005, Vol. 19, No. 6; Ammoxidation of 2-picoline catalyzed by modified $V_2O_5/TiO_2$, *Monatshefte für chemie-chemical monthly*, 2014, Vol. 145, No. 8; Study on the technologic process of synthesis of chromium 2-picolinate, *Chemical Engineer*, 2004, No. 1; The preparation of isonicotinic and picolinic acids, *Journal of American Chemistry Society*, 1952, Vol. 74, No. 21; Studies on the conditions of synthesis of picolinic acid by heterogeneous catalytic oxidation of 2-picoline, *Catalysis Letters*, 1998, Vol. 54, No. 1; and Feed additive chromium picolinate, *Chinese NY Industry Standard*, NY/T 916-2004.

SUMMARY

In order to obtain qualified pyridine-2-carbonitrile products, the oxidation products derived from the production of pyridine-2-carbonitrile through catalytic ammoxidation are often required to be rectified, thereby leading to a large number of rectification residues. With the aim to make full use of the rectification residues to achieve the reduction and harmlessness of the 2-OP rectification residues, a method of preparing pyridine-2-carboxylic acid using 2-OP rectification residues is provided by the application, which is expected to promote the clean and green production of pyridine-2-carbonitrile, improving the utilization efficiency of resources.

High-boiling compounds in the 2-OP rectification residues undergo catalytic pyrolysis in the presence of a phosphorylated zeolite and/or a phosphorylated silica gel to depolymerize to form pyridine-2-carboxamide with a relatively low boiling point. Then, based on the difference in the boiling points, pyridine-2-carboxamide and the unpyrolyzed high-boiling compounds in the 2-OP rectification residues are preliminarily separated by vacuum distillation, and the resulting distillate containing pyridine-2-carboxamide is cooled and crystallized at room temperature and centrifuged or filtered to enable the separation of pyridine-2-carboxamide and the organic substances having a low melting point, thereby producing a crude pyridine-2-carboxamide product. The crude pyridine-2-carboxamide product is refined and purified through recrystallization in water and adsorption by activated carbon to give a refined pyridine-2-carboxamide based on the change of solubility of pyridine-2-carboxamide in water and the adsorption of activated carbon to organic impurities. The refined pyridine-2-carboxamide is mixed with an aqueous sodium hydroxide solution and heated under reflux to produce an aqueous solution containing sodium pyridine-2-carboxylate. The aqueous solution containing sodium pyridine-2-carboxylate is adjusted to pH 3.0-8.5 with a dilute sulfuric acid or hydrochloric acid, added with chromium(III) chloride, chromium(III) nitrate or chromium(III) sulfate for complexation to produce a slurry containing chromium(III) pyridine-2-carboxylate, which is separated by centrifugation or filtration, washed with water and acetone and dried to obtain chromium(III) pyridine-2-carboxylate product.

The chromium(III) pyridine-2-carboxylate product prepared by the invention has a mass percentage of 98.5% or more and a yield is 50% or more based on the weight of the 2-OP rectification residues.

DETAILED DESCRIPTION OF EMBODIMENTS

Figure 1:
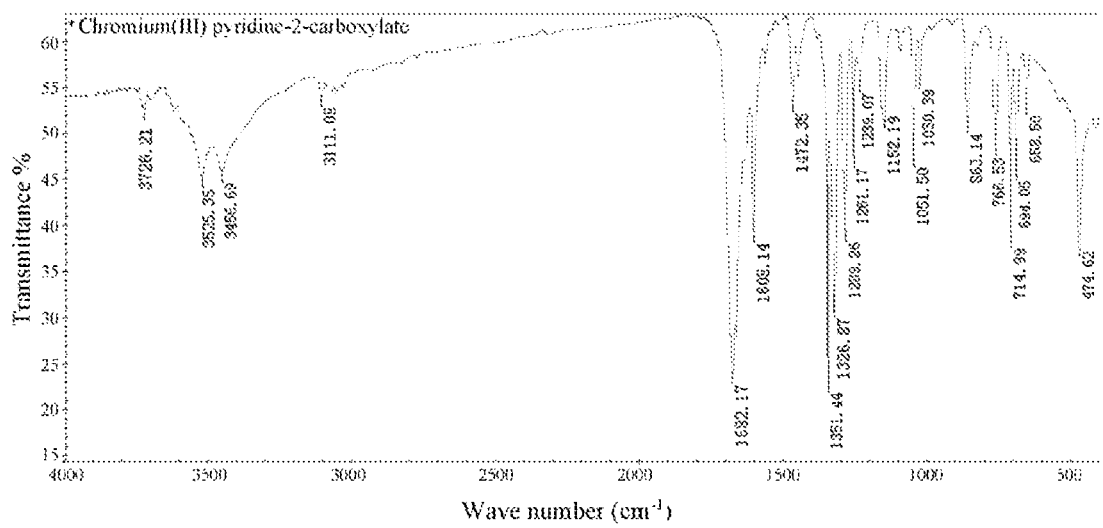
FIG. 1 shows FTIR spectroscopy of chromium(III) pyridine-2-carboxylate.
Figure 2:
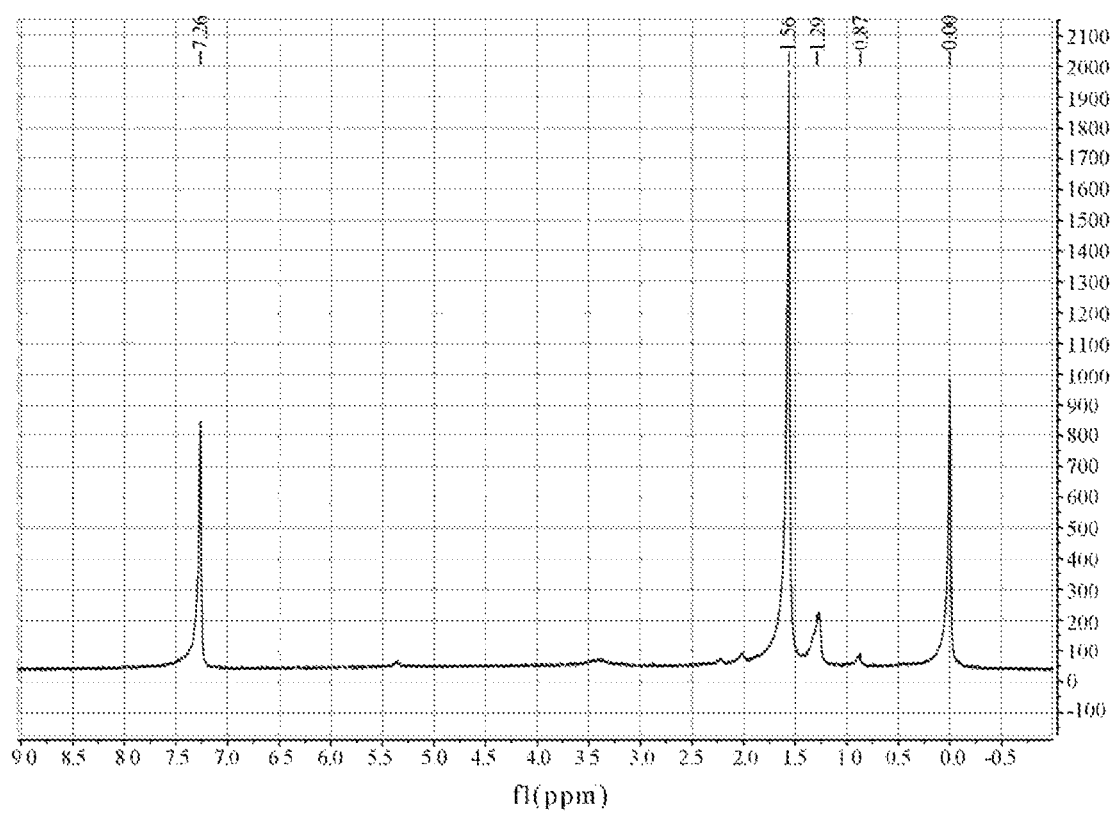
FIG. 2 shows $^1H$ NMR spectroscopy of chromium(III) pyridine-2-carboxylate.

The application discloses a method of preparing chromium(III) pyridine-2-carboxylate using 2-OP rectification residues, including:

sequentially subjecting the 2-OP rectification residues to in-situ catalytic pyrolysis in the presence of a catalyst and vacuum distillation, crystallization at room temperature and separation, recrystallization and dehydration, alkali-catalyzed hydrolysis, acidification and complexation, and separation, washing and drying to prepare chromium(III) pyridine-2-carboxylate of the following formula:

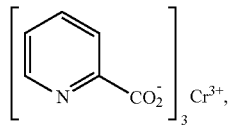

where the catalyst is a phosphorylated zeolite and/or a phosphorylated silica gel.

(1) In-Situ Catalytic Pyrolysis and Vacuum Distillation of 2-OP Rectification Residues A zeolite or a silica gel was immersed in a 10-80 wt % aqueous phosphoric acid solution for 2-48 h and filtered to remove a liquid phase and collect a solid. The solid was burned in a muffle furnace at 300° C.-800° C. for 2-12 h and pulverized to produce the phosphorylated zeolite and/or the phosphorylated silica gel. The phosphorylated zeolite or the phosphorylated silica gel and the 2-OP rectification residues were added to a rector in a weight ratio of 1-10:10-1,000, and subjected to the in-situ catalytic pyrolysis at 240° C.-400° C. and the vacuum distillation at a vacuum degree of 0.01 MPa-0.1 MPa under stirring to obtain a distillate containing pyridine-2-carboxamide, where a yield was 60%-90% based on the weight of the 2-OP rectification residues.

(2) Room-Temperature Crystallization and Separation

The distillate containing pyridine-2-carboxamide was stirred at room temperature and gradually cooled to crystallize. After the distillate was cooled to 30° C. and was fully crystallized, the crystallized product was separated by centrifugation or filtration to obtain a crude solid containing pyridine-2-carboxamide and a small amount of centrifugate or filtrate, where a yield was 55%-85% based on the weight of the 2-OP rectification residues. The crude solid is used to prepare a pyridine-2-carboxamide product, and the centrifugate or filtrate is used in the preparation of pyridine-2-carbonitrile.

(3) Recrystallization and Dehydration

The crude solid containing pyridine-2-carboxamide was mixed with distilled water or deionized water in a weight ratio of 1:1-50, heated under stirring to boiling and added with activated carbon, where a weight ratio of the activated carbon to the crude solid containing pyridine-2-carboxamide was 1:1-100. The reaction mixture was heated again to gentle boiling and the gentle boiling was kept for 5-30 min. Then the reaction mixture was filtered when it was hot to obtain a filtrate. The filtrate was cooled with ice water or frozen brine to a temperature below 20° C. for complete crystallization of pyridine-2-carboxamide. The reaction mixture was separated by centrifugation or filtration to produce a solid. The solid was washed 2-3 times with a small amount of ice water and fully dehydrated by centrifugation or filtration to obtain a wet pyridine-2-carboxamide product, where a yield was 70%-80% based on the weight of the 2-OP rectification residues.

(4) Alkali-Catalyzed Hydrolysis

The wet pyridine-2-carboxamide product was fully mixed with a 5-50 wt % aqueous sodium hydroxide solution and heated under reflux for 0.5-5.0 h to obtain an aqueous solution containing sodium pyridine-2-carboxylate, where a weight ratio of the wet pyridine-2-carboxamide product to sodium hydroxide was 1:0.2-2.0.

(5) Acidification and Complexation

The aqueous solution containing sodium pyridine-2-carboxylate was cooled to a temperature below 50° C., adjusted to pH 3.0-8.5 with a dilute sulfuric acid or a dilute hydrochloric acid and batchwise added with chromium(III) chloride, chromium(III) nitrate or chromium(III) sulfate for complexation at 20-70° C. to obtain a slurry containing chromium(III) pyridine-2-carboxylate.

(6) Separation, Washing and Drying

The slurry containing chromium(III) pyridine-2-carboxylate was separated by centrifugation or filtration to obtain a wet solid product. The wet solid product was sequentially washed with an aqueous solution having a pH of 5.0-6.8 and acetone, and dried at 50-80° C. for 2-12 h to obtain a chromium(III) pyridine-2-carboxylate product.

The application discloses a method of preparing chromium(III) pyridine-2-carboxylate using 2-OP rectification residues, including:

sequentially subjecting the 2-OP rectification residues to in-situ catalytic pyrolysis in the presence of a catalyst and vacuum distillation, crystallization at room temperature and separation, recrystallization and dehydration, alkali-catalyzed hydrolysis, acidification and complexation, and separation, washing and drying.

(1) In-Situ Catalytic Pyrolysis and Vacuum Distillation of 2-OP Rectification Residues The catalyst used in the in-situ catalytic pyrolysis was a phosphorylated zeolite and/or a phosphorylated silica gel, where the zeolite was selected from 4A zeolite, mordenite and HZSM-5 zeolite, and the silica gel was selected from original-color silica gel, allochroic silica gel, silica gel H and silica gel G. The phosphorylated zeolite or the phosphorylated silica gel was prepared as follows. A zeolite or a silica gel was immersed in a 10-80 wt % aqueous phosphoric acid solution for 2-48 h and filtered to remove a liquid phase and collect a solid. The solid was burned in a muffle furnace at 300° C.-800° C. for 2-12 h and pulverized to produce the phosphorylated zeolite or the phosphorylated silica gel having a particle size of 50-300 mesh. The phosphorylated zeolite and/or the phosphorylated silica gel and the 2-OP rectification residues were added to a rector in a weight ratio of 1-10:10-1,000, and subjected to the in-situ catalytic pyrolysis at 240° C.-400° C. and the vacuum distillation at a vacuum degree of 0.01 MPa-0.1 MPa under stirring to obtain a distillate containing pyridine-2-carboxamide, where a yield was 60%-90% based on the weight of the 2-OP rectification residues.

(2) Room-Temperature Crystallization and Separation

The distillate containing pyridine-2-carboxamide was stirred at room temperature and gradually cooled to crystallize. After the distillate was cooled to 30° C. and was fully crystallized, the crystallized product was separated by centrifugation or filtration to obtain a crude solid containing pyridine-2-carboxamide and a small amount of centrifugate or filtrate, where the crude solid had a yield of 55%-85% based on the weight of the 2-OP rectification residues, and can be used to prepare a pyridine-2-carboxamide product, and the centrifugate or filtrate had a yield of 3%-15% based on the weight of the 2-OP rectification residues, and can be used in the preparation of pyridine-2-carbonitrile.

(3) Recrystallization and Dehydration

The crude solid containing pyridine-2-carboxamide was mixed with distilled water or deionized water in a weight ratio of 1:1-50, heated under stirring to boiling and added with activated carbon, where a weight ratio of the activated carbon to the crude solid containing pyridine-2-carboxamide was 1:1-100. The reaction mixture was heated again to gentle boiling and the gentle boiling was kept for 5-30 min. Then the reaction mixture was filtered when it was hot to obtain a filtrate. The filtrate was cooled with ice water or frozen brine to a temperature below 20° C. for complete crystallization of pyridine-2-carboxamide. The reaction mixture was separated by centrifugation or filtration to produce a solid. The solid was washed 2-3 times with a small amount of ice water and fully dehydrated by centrifugation or filtration to obtain a wet pyridine-2-carboxamide product, where a yield was 70%-80% based on the weight of the 2-OP rectification residues.

(4) Alkali-Catalyzed Hydrolysis

The wet pyridine-2-carboxamide product was fully mixed with a 5-50 wt % aqueous sodium hydroxide solution and heated under reflux for 0.5-5.0 h to obtain an aqueous solution containing sodium pyridine-2-carboxylate, where a weight ratio of the wet pyridine-2-carboxamide product to sodium hydroxide was 1:0.2-2.0.

(5) Acidification and Complexation

The aqueous solution containing sodium pyridine-2-carboxylate was cooled to a temperature below 50° C., adjusted to pH 3.0-8.5 with a 5-50 wt % dilute sulfuric acid or a 3-30 wt % dilute hydrochloric acid and batchwise added with chromium(III) chloride, chromium(III) nitrate or chromium (III) sulfate for complexation at 20-70° C. to obtain a slurry containing chromium(III) pyridine-2-carboxylate.

(6) Separation, Washing and Drying

The slurry containing chromium(III) pyridine-2-carboxylate was separated by centrifugation or filtration to obtain a wet solid product. The wet solid product was sequentially washed with an aqueous solution having a pH of 5.0-6.8 and acetone, and dried at 50-80° C. for 2-12 h to obtain a chromium(III) pyridine-2-carboxylate product, where the a yield was greater than 50% based on the weight of the 2-OP rectification residues and a mass fraction of chromium(III) pyridine-2-carboxylate was 98.5% or more.

What is claimed is:

1. A method of preparing chromium(III) pyridine-2-carboxylate using 2-OP rectification residues, comprising:
   sequentially subjecting the 2-OP rectification residues to in-situ catalytic pyrolysis in the presence of a catalyst and vacuum distillation, crystallization at room temperature and separation, recrystallization and dehydration, alkali-catalyzed hydrolysis, acidification and complexation, and separation, washing and drying to produce chromium(III) pyridine-2-carboxylate of the following formula:

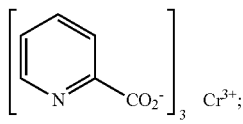

wherein the catalyst is a phosphorylated zeolite.

2. The method of claim 1, wherein the phosphorylated zeolite is prepared by a method comprising steps of:
   immersing a zeolite in a 10-80 wt % aqueous phosphoric acid solution for 2-48 h followed by filtration to remove a liquid phase and collect a solid;
   burning the solid in a muffle furnace at 300° C.-800° C. for 2-12 h; and
   pulverizing the burned solid to obtain the phosphorylated zeolite.

3. The method of claim 1, wherein the in-situ catalytic pyrolysis and vacuum distillation comprises:

adding the phosphorylated zeolite and the 2-OP rectification residues to a reactor in a weight ratio of 1-10: 10-1,000; and performing the in-situ catalytic pyrolysis at 240° C.-400° C. and the vacuum distillation at a vacuum degree of 0.01 MPa-0.1 MPa under stirring to obtain a distillate containing pyridine-2-carboxamide; wherein a yield of the distillate containing pyridine-2-carboxamide is 60%-90% based on the weight of the 2-OP rectification residues.

4. The method of claim 2, wherein the zeolite is selected from 4A zeolite, mordenite and HZSM-5 zeolite.

5. The method of claim 2, wherein the phosphorylated zeolite has a particle size of 50-300 mesh.

6. The method of claim 1, wherein a temperature for in-situ catalytic pyrolysis is 240° C.-400° C. and a vacuum degree for the vacuum distillation is 0.01 MPa-0.1 MPa.

7. The method of claim 3, wherein the crystallization at room temperature and separation comprises:
   gradually stirring the distillate containing pyridine-2-carboxamide at room temperature followed by cooling for crystallization; and after the distillate is cooled to 30° C. and is fully crystallized, separating the crystallized product by centrifugation or filtration to obtain a crude solid containing pyridine-2-carboxamide; wherein a yield of the crude solid containing pyridine-2-carboxamide is 55%-85% based on the weight of the 2-OP rectification residues.

8. The method of claim 7, wherein the recrystallization and dehydration comprises:
   mixing the crude solid containing pyridine-2-carboxamide with distilled water or deionized water in a weight ratio of 1:1-50; heating the reaction mixture under stirring to boiling; adding activated carbon to the reaction mixture;
   heating the reaction mixture again to gentle boiling and keeping the gentle boiling for 5-30 min; filtering the reaction mixture when it is hot to obtain a filtrate; cooling the filtrate with ice water or frozen brine to a temperature below 20° C. to allow for complete crystallization of pyridine-2-carboxamide;
   separating the reaction mixture by centrifugation or filtration to produce a solid; washing the solid 2-3 times with a small amount of ice water; and
   fully dehydrating the washed solid by centrifugation or filtration to obtain a wet pyridine-2-carboxamide product;
   wherein a yield of the wet pyridine-2-carboxamide product is 70%-80% based on the weight of the 2-OP rectification residues, and a weight ratio of the activated carbon to the crude solid containing pyridine-2-carboxamide is 1:1-100.

9. The method of claim 8, wherein the alkali-catalyzed hydrolysis comprises:
   fully mixing the wet pyridine-2-carboxamide product with a 5-50 wt % aqueous sodium hydroxide solution; and
   heating the reaction mixture under reflux for 0.5-5.0 h to obtain an aqueous solution containing sodium pyridine-2-carboxylate;
   wherein a weight ratio of the wet pyridine-2-carboxamide product to sodium hydroxide is 1:0.2-2.0.

10. The method of claim 9, wherein the acidification and complexation comprises:
   cooling the aqueous solution containing sodium pyridine-2-carboxylate to a temperature below 50° C.; and adjusting the cooled aqueous solution containing sodium pyridine-2-carboxylate to pH 3.0-8.5 with a 5-50 wt % dilute sulfuric acid or a 3-30 wt % dilute hydrochloric acid followed by batchwise addition of chromium(III) chloride, chromium(III) nitrate or chromium(III) sulfate for complexation at 20-70° C. to obtain a slurry containing chromium(III) pyridine-2-carboxylate.

11. The method of claim 10, wherein the separation, washing and drying comprises:
    separating the slurry containing chromium(III) pyridine-2-carboxylate by centrifugation or filtration to obtain a wet solid product;
    washing the wet solid product sequentially with an aqueous solution having a pH of 5.0-6.8 and acetone; and
    drying the washed wet solid product at 50-80° C. for 2-12 h to obtain a chromium(III) pyridine-2-carboxylate product.

* * * * *